United States Patent [19]

Prucher et al.

[11] Patent Number: 5,698,553
[45] Date of Patent: Dec. 16, 1997

[54] BENZYLPIPERIDINE DERIVATIVES

[75] Inventors: Helmut Prucher, Heppenheim; Rudolf Gottschlich, Beinheim; Joachim Leibrock, Griesheim; Harry Schwartz, Hofheim-Deidenbergen, all of Germany

[73] Assignee: Merck Patent Gesellschaft Mit Beschrankter Haftung, Darmstadt, Germany

[21] Appl. No.: 550,105

[22] Filed: Oct. 30, 1995

[30] Foreign Application Priority Data

Oct. 31, 1994 [DE] Germany ............ P 44 38 810.1
Jul. 19, 1995 [DE] Germany ............ 195 26 269.7

[51] Int. Cl.⁶ .................. C07D 401/06; A61K 31/445
[52] U.S. Cl. .................. 514/222.8; 540/523; 540/521; 544/48; 544/50; 544/92; 546/198; 546/199; 546/200; 546/201; 514/227.2; 514/230.5; 514/258; 514/321; 514/322; 514/323; 514/324
[58] Field of Search .................. 546/198, 199, 546/200, 201; 540/521, 523; 544/48.5, 92

[56] References Cited

U.S. PATENT DOCUMENTS

| | | | |
|---|---|---|---|
| 4,455,422 | 6/1984 | Banno et al. | 544/363 |
| 4,468,402 | 8/1984 | Tominaga et al. | 514/312 |
| 5,034,401 | 7/1991 | Frost et al. | 514/323 |
| 5,304,401 | 4/1994 | Frost et al. | 514/323 |
| 5,455,422 | 10/1995 | Banno et al. | 544/363 |

FOREIGN PATENT DOCUMENTS 351282  3/1989  European Pat. Off.
2688504 3/1992  France.

OTHER PUBLICATIONS

Chenard, B.L., Butler, T.W., Shalaby, I. A., Prochniak, M. A., Koe, B. K., Fox, C. B., "Oxindole N-methyl-d-aspartate (NMDA) Antagonists", Bioorg.&Med.Chem.Let., 3(1), pp. 91–94, Jan. 1993.
Chemical Abstracts, vol. 118, 1993.
Patent Abstracts of Japan, vol. 006, No. 239, 1982.
Chemical Abstract 98:143285f, 1983.
Chemical Abstract 96:85434z, 1982.

Primary Examiner—C. Warren Ivy
Assistant Examiner—Lyman H. Smith
Attorney, Agent, or Firm—Millen, White, Zelano & Branigan, P.C.

[57] ABSTRACT

A benzylpiperidine compound of formula I

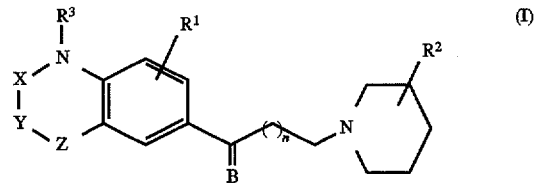

in which
  $R^1$ is H, Hal or nitro,
  $R^2$ is a benzyl group, which is unsubstituted or substituted by Hal on the aromatic portion, in the 2-, 3- or 4-position of the piperidine ring, with the proviso that $R^2$ is not in the 4-position if X is —CO—, Y and Z are —CH₂ and $R^1$ is H,
  $R^3$ is H or A,
  X is —O—, —S—, —NH—, —CO— or —SO₂—,
  Y is —CH₂—, —NH—, —O—, —S—, —NH— or alternatively —CO— if X is —CO— and Z is —NH— or —NA—,
  Z is —CH₂—, —C(A)₂—, —CH₂CH₂—, —CH=CH—, —CO—, —NH—, —NA—, —O—, —S— or a bond,
wherein X—Y or Y—Z is not —O—, —S—S—, —NH—O—, —O—NH—, —NH—NH—, —O—S— or —S—O,
  A is alkyl having 1–6 C atoms,
  B is O or both H and OH, i.e.,

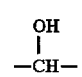

together with the carbon atom to which B is bonded,
  Hal is F, Cl, Br or I and
  n is 0, 1 or 2
or a physiologically acceptable salt thereof,
and their salts show a high affinity for binding sites of amino acid receptors and are suitable for the treatment of neurodegenerative disorders.

14 Claims, No Drawings

BENZYLPIPERIDINE DERIVATIVES

The invention relates to novel benzylpiperidine

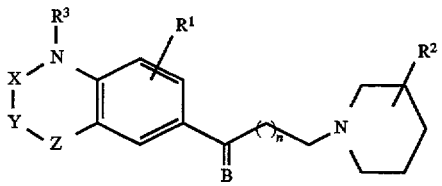 (I)

in which

R¹ is H, Hal or nitro,

R² is a benzyl group, which is unsubstituted or substituted by Hal on the aromatic portion, in the 2-, 3- or 4-position of the piperidine ring, with the proviso that R²≠4-benzyl, i.e., R² is not in the 4-position of the piperidine ring, if X is —CO—, Y and Z are —CH₂ and R¹ is H, R³ is H or A, X is —O—, —S—, —NH—, —CO— or —SO₂—, Y is —CH₂—, —O—, —S—, —NH— or alternatively —CO— if X is —CO— and Z is —NH— or —NA—, Z is —CH₂—, —C(A)₂—, —CH₂CH₂—, —CH=CH—, —CO—, —NH—, —NA—, —O—, —S— or a bond, wherein X—Y or Y—Z is not —O—O—, —S—S—, —NH—O—, —O—NH—, —NH—NH—, —O—S— or —S—O—, A is alkyl having 1-6 C atoms, B is O or both H and OH, i.e.,

together with the carbon atom to which B is bonded,

Hal is F, Cl, Br or I and n is 0, 1 or 2 and their salts.

The invention was based on the object of finding novel compounds having useful properties, in particular those which can be used for the preparation of medicaments. Compounds analogous to formula I, wherein R₂ is 4-benzyl, are disclosed in CA 98:143,285 and CA 96: 85,434.

It has been found that the compounds of the formula I and their physiologically acceptable salts have useful pharmacological properties. They show a high affinity for binding sites of amino acid receptors, in particular for the glycine, polyamine and/or NMDA binding site of the NMDA receptor (NMDA=N-methyl-D-aspartate). The compounds are therefore suitable for the treatment of neurodegenerative disorders including cerebrovascular diseases. The novel active compounds can also be used as analgesics or anxiolytics as well as for the treatment of epilepsy, schizophrenia, Alzheimer's, Parkinson's or Huntingdon's disease, cerebral ischaemias or infarctions. They are also suitable for the treatment of psychoses caused by excessive amino acid levels. All of the above compounds have each of the above utilities, to a finite extent.

The [³H]-CGP-39653 binding test for the glutamate binding site of the NMDA receptor can be carried out, for example, according to the method of M. A. Stills et al., described in Eur. J. Pharmacol. 192, 19–24 (1991). The test for the glycine binding site of the NMDA receptor can be carried out by the method of M. B. Baron et al., described in Eur. J. Pharmacol. 206, 149–154 (1991). The in vitro amino acid release can be determined according to the method of D. Lobner and P. Lipton (Neurosci. Lett. 117, 169–174 (1990)).

The action against Parkinson's disease, i.e. the potentiation of the L-DOPA-induced contralateral rotation in hemiparkinson rats, can be determined by the method of U. Ungerstedt and G. W. Arbuthnott, Brain Res 24, 485 (1970).

The compounds are particularly suitable for the treatment or prophylaxis of strokes, and for protection from and for the treatment of cerebral edemas and undersupply conditions of the central nervous system, in particular hypoxia or anoxia.

The actions mentioned can additionally be determined or investigated by methods such as are described in the following references:

J. W. McDonald, F. S. Silverstein and M. v. Johnston, Eur. J. Pharmacol. 140, 359 (1987); R. Gill, A. C. Foster and G. N. Woodruff, J. Neurosci. 7, 3343 (1987); S. M. Rothmann, J. H. Thurston, R. E. Hauhart, G. D. Clark and J. S. Soloman, Neurosci. 21, 73 (1987) or M. P. Goldbert, P.-C. Pham and D. W. Choi, Neurosci. Lett. 80, 11 (1987).

The compounds can therefore be used as pharmaceutical active compounds in human and veterinary medicine. They are also suitable as intermediates for the preparation of other compounds having useful properties.

The invention relates to compounds of the formula I and their salts.

The group A is alkyl having 1, 2, 3, 4, 5 or 6 C atoms, in particular methyl or ethyl, but also propyl, isopropyl, butyl, isobutyl, sec-butyl or tert-butyl.

The group Hal is preferably Cl, furthermore preferably F.

The radical R¹ is preferably H or Cl.

The radical R² is preferably unsubstituted benzyl, also preferably 2-, 3- or 4-fluorobenzyl, and furthermore 2-, 3- or 4-chlorobenzyl, 2-, 3- or 4-bromobenzyl, or 2-, 3- or 4-iodobenzyl.

The radical X is preferably —CO—.

The radical Y is preferably —NH—, also preferably —CH₂— or —O—.

The radical Z is preferably a bond, also preferably —CH₂—, —C(CH₃)₂— or —O—.

Accordingly the group —X—Y—Z— is preferably —CO—NH—, also preferably —CO—CH₂—CH₂—, —CO—CH₂—C(CH₃)₂—, —CO—CH₂—O—, —CO—O—CH₂—, —CO—NH—CH₂—, or —CO—O—, and also —CO—S— or CO—CH₂—.

The invention accordingly relates in particular to those compounds of the formula I in which at least one of the radicals mentioned has one of the preferred meanings indicated above. Some preferred groups of compounds can also be expressed by the formulae Ia to Ih below, which correspond to the formula I and in which the radicals not indicated in greater detail have the meaning given under the formula I, but in which in Ia R¹ is H;

in Ib R¹ is H or Cl;

in Ic —X—Y—Z— is —CO—NH—, —CO—CH₂—CH₂—, —CO—CH₂—C(CH₃)₂—, —CO—CH₂—O—, —CO—O—CH₂—, —CO—NH—CH₂— or —CO—O—, and also —CO—S— or —CO—CH₂—;

in Id —X—Y—Z— is —CO—NH—, —CO—CH₂—CH₂— or —CO—CH₂—C(CH₃)₂—;

in Ie —X—Y—Z— is —CO—NH— or —CO—CH₂—CH₂—;

in If R¹ is H or Cl and —X—Y—Z— is —CO—NH—, —CO—CH₂—CH₂— or —CO—CH₂—C(CH₃)₂—;

in Ig R¹ is H or Cl and —X—Y—Z— is —CO—NH—
or —CO—CH₂—CH₂—;

in Ih R¹ is H and —X—Y—Z— is —CO—NH—.

Compounds which are furthermore preferred are those of the formulae I' and Ia' to Ih' which correspond to the formulae I or Ia to Ih, but in which R² is an unsubstituted benzyl group.

The invention further relates to a process for the preparation of benzylpiperidine derivatives of the formula I indicated above and also of their salts, characterized in that a compound which otherwise corresponds to the formula I, but which instead of one or more H atoms contains one or more reducible groups and/or one or more additional bonds, is treated with a reducing agent,
or in that a compound of the formula II

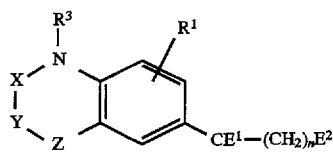

in which

E¹ is O or H and OH

E² is Cl, Br, I or a reactive esterified OH group or

E¹ and E² together can be an O atom and

R¹, R³, X, Y,

Z and n have the meanings indicated, is reacted with a compound of the formula III

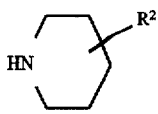

in which

R² has the meaning indicated, and/or in that a base of the formula I which is obtained is converted into one of its acid addition salts by treating with an acid.

As a rule, the compounds of the formula I are prepared by methods known per se, as are described in the literature (e.g. in the standard works such as Houben-Weyl, Methoden der Organischen Chemie (Methods of Organic Chemistry), Georg-Thieme-Verlag, Stuttgart or in J. March, Adv. Org. Chem., 3rd Ed., J. Wiley & Sons (1985)), namely under reaction conditions which are known and suitable for the reactions mentioned. Use can also be made here of variants which are known per se, but not mentioned here in greater detail.

As a rule, the starting substances are known, or they can be prepared in analogy to known substances by methods known per se. If desired, they can also be formed in situ such that they are not isolated from the reaction mixture, but are immediately reacted further to give the compounds of the formula I.

On the other hand, it is possible to carry out the reaction stepwise, it being possible to isolate further intermediates.

The individual process variants are illustrated in greater detail in the following.

Compounds of the formula I in which B is Hand OH are preferably prepared by reduction of appropriate precursors which contain reducible groups and/or additional bonds. Preferably they are prepared from the corresponding ketones of the formula IV

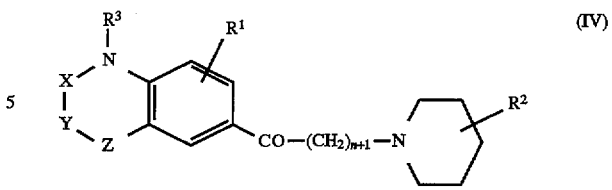

in which

R¹, R², R³, X, Y, Z and n have the meanings indicated under formula I.

They and the ketones defined by formula I are obtainable, for example, by Friedel-Crafts acylation of the compounds, which as a rule are known, of the formula V

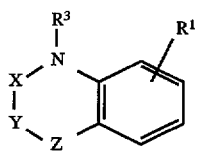

with appropriate end-chlorinated alkylcarbonyl chlorides, in particular with chloroacetyl chloride, 1-chloropropionyl chloride or with 1-chlorobutyryl chloride, and subsequent reaction with a 2-, 3- or 4-R²-piperidine of the formula III.

Suitable reducing agents are preferably catalytically activated or nascent hydrogen and also complex metal hydrides, e.g. alkali metal alumino-hydrides or alkali metal borohydrides.

Suitable catalysts for catalytic hydrogenations are preferably noble metal catalysts such as platinum or palladium, which can be present on a support such as carbon, and also Raney metals such as Raney nickel or copper/chromium oxide. Hydrogenations are expediently carried out at pressures between 0 and 200 bar and at temperatures between 0° and 150°, in particular between 15° and 100°.

Suitable solvents are, for example, alcohols such as methanol, ethanol or isopropanol, ethers such as tetrahydrofuran (THF) or methyl tert-butyl ether, esters such as ethyl acetate, amides such as dimethylformamide (DMF), or sulfoxides such as dimethyl sulfoxide (DMSO).

Reduction of the ketones IV with a complex metal hydride, in particular NaBH₄, is preferred. This is expediently performed in an alcohol such as methanol at temperatures between 0° and 30°, preferably 5° and 15°. In the case of poorly soluble starting substances, addition of a further solvent such as THF is recommended. The reducing agent is expediently employed in a large excess, e.g. in the molar ratio 1:1.

In the reduction of the ketones IV, a mixture of the two epimeric hydroxy compounds as a rule results. If a chiral reducing agent is used, e.g. (+)- or (−)-β-chlorodiisopinocamphenylborane, one of the epimers can also be obtained preferably or exclusively. The same thing takes place as a result of reductions with microorganisms suitable for this purpose, in particular those of the genera Candida or Rhodutorula, e.g. Rhodutorula mucilaginosa.

Compounds of the formula I in which B is H and OH are also obtainable by reaction of halohydrins or epoxides of the formula II with 2-, 3- or 4-R²-piperidines of the formula III.

The starting substances of the formula II are obtainable, for example, by the said Friedel-Crafts acylation of compounds of the formula V and, if appropriate, subsequent reduction and also, if desired, elimination of HCl with epoxide formation.

As a rule, compounds of the formula III are known and commercially available.

The reaction of II with III expediently takes place in the presence or absence of one of the solvents mentioned in the presence or absence of a condensing agent, e.g. of a base, at temperatures between −20° and 200°, preferably 0° and 100°. Suitable bases are, for example, alkali metal hydroxides such as NaOH or KOH, alkali metal carbonates such as $Na_2CO_3$ or $K_2CO_3$, or tertiary amines such as triethylamine or pyridine. Ethanol is particularly preferred as a solvent, triethylamine as a base.

A base of the formula I can be converted into the associated acid addition salt using an acid. For this reaction, suitable acids are those which give physiologically acceptable salts. Inorganic acids can thus be used, e.g. sulfuric acid, nitric acid, halohydric acids such as hydrochloric acid or hydrobromic acid, phosphoric acids such as orthophosphoric acid, sulfamic acid, and also organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, and laurylsulfuric acid. Salts with physiologically unacceptable acids, e.g. picrates, can be used for the purification of the compounds of the formula I.

The free bases of the formula I can, if desired, be set free from their salts by treatment with strong bases such as sodium or potassium hydroxide, or sodium or potassium carbonate.

The compounds of the formula I have at least two center of asymmetry if $R^2$ is 2- or 3-benzyl and B is H+OH. In their preparation they can therefore be obtained as a mixture of racemates or, if optically active starting substances are used, alternatively in optically active form. The individual racemates can be isolated from the racemate mixtures in pure form, for example by recrystallizing from inert solvents. Racemates which are obtained can be separated, if desired, into their enantiomers mechanically or chemically by methods known per se. Preferably, diastereomers are formed from the racemate by reaction with an optically active resolving agent. Suitable resolving agents are, for example, optically active acids, such as the D- and L-forms of tartaric acid, dibenzoyltartaric acid, diacetyltartaric acid, camphorsulfonic acids, mandelic acid, malic acid or lactic acid. The various forms of the diastereomers can be separated in a manner known per se, e.g. by fractional crystallization, and the optically active compounds of the formula I can be set free from the diastereomers in a manner known per se.

The invention also relates to the use of the compounds of the formula I and their physiologically acceptable salts for the production of pharmaceutical preparations, in particular by non-chemical routes. In this context, they can be brought into a suitable dosage form together with at least one solid, liquid and/or semi-liquid excipient or auxiliary and, if appropriate, in combination with one or more other active compounds.

The invention also relates to pharmaceutical preparations containing at least one compound of the formula I and/or one of its physiologically acceptable salts.

These preparations can be used as medicaments in human or veterinary medicine. Possible carriers are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc and petroleum jelly. Tablets, pills, coated tablets, capsules, powders, granules, syrups, juices or drops are used, in particular, for oral administration, suppositories are used for rectal administration, solutions, preferably oily or aqueous solutions, and also suspensions, emulsions or implants are used for parenteral administration, and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colorants, flavourings and/or aromatic substances. If desired they can also contain one or more other active compounds, e.g. one or more vitamins.

The compounds of the formula I and their physiologically acceptable salts can be used in the control of diseases, in particular of pain conditions, but also for decreasing the damage resulting after an ischemia. The compounds are particularly suitable for the treatment of neurodegenerative disorders or of disorders which are caused by a dysfunction at the glycine, polyamine or glutamate binding site of the NMDA receptor.

As a rule, the substances according to the invention are preferably administered here in doses of between approximately 1 and 500 mg, in particular between 5 and 100 mg per unit dose. The daily dose is preferably between approximately 0.02 and 10 mg/kg of body weight. The specific dose for each intended patient, however, depends on a wide variety of factors, for example on the efficacy of the specific compound employed, on age, body weight, general state of health and sex, on the diet, on the time and route of administration, on the excretion rate, the pharmaceutical combination and the severity of the particular disorder to which the therapy applies. Oral administration is preferred.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application Nos. P 44 38 810.1, filed Oct. 31, 1994, and DE 19526269.7, filed Jul. 7, 1995, are hereby incorporated by reference. The symbols "S" and "R" relate to the chiral C atom in the piperidine ring, if not stated otherwise.

In the following examples "customary working up" means: if necessary, water or dilute sodium hydroxide solution is added, the mixture is extracted with dichloromethane, the organic phase is separated off, dried with sodium sulfate, filtered and evaporated, and the residue is purified by chromatography on silica gel and/or by crystallization. $[\alpha]=[\alpha]_D^{20}$, c=1 in DMSO.

EXAMPLES

Example 1

A solution of 36.2 g of 1,2,3,4-tetrahydro-6-(2-(3-benzylpiperidino)-1-oxoethyl)quinolin-2-one ("A"; racemate; obtainable by reaction of 1,2,3,4-tetrahydroquinolin-2-one with chloroacetyl chloride/$AlCl_3$/DMF to give 6-chloroacetyl-1,2,3,4-tetrahydroquinolin-2-one ("B") and subsequent reaction with (racemic) 3-benzylpiperidine in ethanol in the presence of triethylamine) in 725 ml of methanol is treated with 3.8 g of NaBH$_4$ and then stirred at 10° for 2 hours. Customary working up (sodium hydroxide solution/dichloromethane) gives 6-(2-(3-benzylpiperidino)-1-hydroxyethyl)-1,2,3,4-tetrahydroquinolin-2-one, racemate ("C").

The following are obtained analogously using NaBH$_4$:

from (S)-"A" (m.p. 155°–157°; [α] +18.8°; obtainable from "B" and 3S-benzylpiperidine):
(S)-"C"; hydrochloride, m.p. 209°–211°; [α] +30.4°;

from (R)-"A" (obtainable from "B" and 3R-benzylpiperidine):
(R)-"C"; m.p. 136°–138°; hydrochloride, m.p. 209°–211°; [α]–37.5°;

from 1,2,3,4-tetrahydro-6-(2-(2-benzylpiperidino)-1-oxoethyl)quinolin-2-one ("D"; racemate; obtainable by reaction of "B" with 2-benzylpiperidine):
6-(2-(2-benzylpiperidino)-1-hydroxyethyl)-1,2,3,4-tetrahydroquinolin-2-one, racemate ("E");

from (S*)-"D" (obtainable from "B" and 2S,-benzylpiperidine):
(S*)-"E", resin;

from (R*)-"D" (obtainable from "B" and 2R*-benzylpiperidine):
(R*)-"E", resin;

from 7-(2-(3-benzylpiperidino)-1-oxoethyl)-2,3-dihydro-1,4-benzoxazin-3-one ("F"; obtainable by reaction of 2,3-dihydro-1,4-benzoxazin-3-one with chloroacetyl chloride to give 7-chloroacetyl-2,3-dihydro-4H-1,4-benzoxazin-3-one ("G"), then reaction with 3-benzylpiperidine):
7-(2-(3-benzylpiperidino)-1-hydroxyethyl)-2,3-dihydro-4H-1,4-benzoxazin-3-one, racemate ("H");

from (S)-"F" (obtainable from "G" and 3S-benzylpiperidine):
(S)-"H"; hydrochloride, amorphous, dec. at 130°; [α] +25.0°;

from (R)-"F" (obtainable from "G" and 3R-benzylpiperidine):
(R)-"H", hydrochloride, amorphous, dec. at 117°; [α] –24.5°;

from 7-(2-(2-benzylpiperidino)-1-oxoethyl)-2,3-dihydro-4H-1,4-benzoxazin-3-one ("I"; racemate; obtainable by reaction of "G" with 2-benzylpiperidine):
7(2-(2-benzylpiperidino)-1-hydroxyethyl)-2,3-dihydro-4H-1,4-benzoxazin-3-one, racemate ("J");

from (S*)-"I" (obtainable from "G" and 2S*-benzylpiperidine):
(S*)-"J", m.p. 132°–135°; [α] –26.0°;

from (R*)-"I" (obtainable from "G" and 2R*-benzylpiperidine):
(R*)-"J", m.p. 135° (dec. at); [α] +27.0°;

from 5-(2-(3-benzylpiperidino)-1-oxoethyl)-2,3-dihydrobenzimidazol-2-one ("K"; obtainable by reaction of 2,3-dihydrobenzimidazol-2-one with chloroacetyl chloride to give 5-chloroacetyl-2,3-dihydrobenzimidazol-2-one ("L"), then reaction with 3-benzylpiperidine):
5-(2-(3-benzylpiperidino)-1-hydroxyethyl)-2,3-dihydrobenzimidazol-2-one, racemate ("M");

from (S)-"K" (obtainable from "L" and 3S-benzylpiperidine):
(S)-"M"; m.p. 164°–167°; [α] +30.7°;

from (R)-"K" (obtainable from "L" and 3R-benzylpiperidine):
(R)-"M"; m.p. 163°–166°; [α] –31.7°;

from 5-(2-(2-benzylpiperidino)-1-oxoethyl)-2,3-dihydrobenzimidazol-2-one ("N"; obtainable by reaction of "L" with 2-benzylpiperidine):
5-(2-(2-benzylpiperidino)-1-hydroxyethyl)-2,3-dihydrobenzimidazol-2-one, racemate ("O");

from (S*)-"N" (obtainable from "L" and 2S*-benzylpiperidine):
(S*)-"O";

from (R*)-"N" (obtainable from "L" and 2R*-benzylpiperidine):
(R*)-"O";

from 6-(2-(3-benzylpiperidino)-1-oxoethyl)-2,3-dihydrobenzoxazol-2-one ("P"; obtainable by reaction of 2,3-dihydrobenzoxazol-2-one with chloroacetyl chloride to give 6-chloroacetyl-2,3-dihydrobenzoxazol-2-one ("Q"), then reaction with 3-benzylpiperidine):
6-(2-(3-benzylpiperidino)-1-hydroxyethyl)-2,3-dihydrobenzoxazol-2-one, racemate ("R");

from (S)-"P" (obtainable from "Q" and 3S-benzylpiperidine):
(S)-"R", amorphous, dec. at 159°; [α] +23.8°;

from (R)-"P" (obtainable from "Q" and 3R-benzylpiperidine):
(R)-"R", amorphous, dec. at 142°; [α] –24.0°.

Example 2

Analogously to Example 1, NaBH$_4$ reduction of the ketones below 6-(2-(3-benzylpiperidino)-1-oxoethyl)-7-chloro-1,2,3,4-tetrahydroquinolin-2-one 6-(2-(3-benzylpiperidino)-1-oxoethyl)-7-chloro-1,2,3,4-tetrahydro-4,4-dimethylquinolin-2-one 6-(2-(2-benzylpiperidino)-1-oxoethyl)-7-chloro-1,2,3,4-tetrahydro-4,4-dimethylquinolin-2-one 6-(2-(3-benzylpiperidino)-1-oxoethyl)-8-chloro-1,2,3,4-tetrahydro-4,4-dimethylquinolin-2-one 6-(2-(3-benzylpiperidino)-1-oxoethyl)-5-chloro-1,2,3,4-tetrahydro-4,4-dimethylquinolin-2-one 6-(2-(3-benzylpiperidino)-1-oxoethyl)-1,2-dihydro-4H-3,1-benzoxazin-2-one 6-(2-(3-benzylpiperidino)-1-oxoethyl)-1,2,3,4-tetrahydroquinazolin-2-one 6-(2-(3-benzylpiperidino)-1-oxoethyl)-2,3-dihydrobenzothiazol-2-one or their enantiomers gives the compounds below:

6-(2-(3-benzylpiperidino)-1-hydroxyethyl)-7-chloro-1,2,3,4-tetrahydroquinolin-2-one 6-(2-(3S-benzylpiperidino)-1-hydroxyethyl)-7-chloro-1,2,3,4-tetrahydroquinolin-2-one 6-(2-(3R-benzylpiperidino)-1-hydroxyethyl)-7-chloro-1,2,3,4-tetrahydroquinolin-2-one 6-(2-(3-benzylpiperidino)-1-hydroxyethyl)-7-chloro-1,2,3,4-tetrahydro-4,4-dimethylquinolin-2-one 6-(2-(3S-benzylpiperidino)-1-hydroxyethyl)-7-chloro-1,2,3,4-tetrahydro-4,4-dimethylquinolin-2-one, hydrochloride, m.p. 221°–222°; [α] +46.8°

6-(2-(3R-benzylpiperidino)-1-hydroxyethyl)-7-chloro-1,2,3,4-tetrahydro-4,4-dimethylquinolin-2-one, hydrochloride, m.p. 201°–203°; [α] –29.1°

6-(2-(2-benzylpiperidino)-1-hydroxyethyl)-7-chloro-1,2, 3,4-tetrahydro-4,4-dimethylquinolin-2-one 6-(2-(2S*-benzylpiperidino)-1-hydroxyethyl)-7-chloro-1, 2,3,4-tetrahydro-4,4-dimethylquinolin-2-one 6-(2-(2R*-benzylpiperidino)-1-hydroxyethyl)-7-chloro-1,2,3,4-tetrahydro-4,4-dimethylquinolin-2-one 6-(2-(3-benzylpiperidino)-1-hydroxyethyl)-8-chloro-1,2, 3,4-tetrahydro-4,4-dimethylquinolin-2-one 6-(2-(3S-benzylpiperidino)-1-hydroxyethyl)-8-chloro-1, 2,3,4-tetrahydro-4,4-dimethylquinolin-2-one 6-(2-(3R-benzylpiperidino)-1-hydroxyethyl)-8-chloro-1, 2,3,4-tetrahydro-4,4-dimethylquinolin-2-one 6-(2-(3-benzylpiperidino)-1-hydroxyethyl)-5-chloro-1,2, 3,4-tetrahydro-4,4-dimethylquinolin-2-one 6-(2-(3S-benzylpiperidino)-1-hydroxyethyl)-5-chloro-1, 2,3,4-tetrahydro-4,4-dimethylquinolin-2-one 6-(2-(3R-benzylpiperidino)-1-hydroxyethyl)-5-chloro-1, 2,3,4-tetrahydro-4,4-dimethylquinolin-2-one 6-(2-(3-benzylpiperidino)-1-hydroxyethyl)-1,2-dihydro-4H-3,1-benzoxazin-2-one 6-(2-(3S-benzylpiperidino)-1-hydroxyethyl)-1,2-dihydro-4H-3,1-benzoxazin-2-one 6-(2-(3R-benzylpiperidino)-1-hydroxyethyl)-1,2-dihydro-4H-3,1-benzoxazin-2-one 6-(2-(3-benzylpiperidino)-1-hydroxyethyl)-1,2,3,4-tetrahydroquinazolin-2-one 6-(2-(3S-benzylpiperidino)-1-hydroxyethyl)-1,2,3,4-tetrahydroquinazolin-2-one; m.p. 157°–160°; [α] +29.7°;

6-(2-(3R-benzylpiperidino)-1-hydroxyethyl)-1,2,3,4-tetrahydroquinazolin-2-one; m.p. 185°–162°; [α] −27.9°;

6-(2-(3-benzylpiperidino)-1-hydroxyethyl)-2,3-dihydrobenzothiazol-2-one 6-(2-(3S-benzylpiperidino)-1-hydroxyethyl)-2,3-dihydrobenzothiazol-2-one 6-(2-(3R-benzylpiperidino)-1-hydroxyethyl)-2,3-dihydrobenzothiazol-2-one Example 3

A solution of 7.1 g of (+)-β-chlorodiisopinocampheylborane in 20 ml of ether is cooled to −70° C. under $N_2$ and treated dropwise with stirring with a solution of 1 g of (S)-"A" in 15 ml of THF. The mixture is stirred for a further 2 hours, allowed to warm to room temperature by standing for 16 hours and treated with aqueous/methanolic hydrochloric acid. The phases are separated, and the aqueous phase is washed with hexane and rendered alkaline with NaOH. Customary working up gives 6-(2-(3S-benzylpiperidino)-1R*-hydroxyethyl)-1,2,3,4-tetrahydroquinolin-2-one, hydrochloride, m.p. 218°–219° (dec.).

Analogously, starting from (S)-"A" with (−)-β-chlorodiisopinocampheylborane gives 6-(2-(3S-benzylpiperidino)-1S*-hydroxyethyl)-1,2,3,4-tetrahydroquinolin-2-one, hydrochloride, m.p. 221°–223°.

Example 4

A solution of 100 mg of (S)-"A" in 10 ml of ethanol is added to a culture of Rhodutorula mucilaginosa in 1000 ml of a nutrient solution which contains 1% yeast extract, 2% peptone from casein, 2% glucose and 0.1% $KH_2PO_4$. The mixture is incubated at 28° for 72 hours with continuous shaking. Customary working up gives 6-(2-(3S-benzylpiperidino)-1S*-hydroxyethyl)-1,2,3,4-tetrahydroquinolin-2-one, hydrochloride, m.p. 221°–223°.

Example 5

A mixture of 18.9 g of 1,2,3,4-tetrahydro-6-oxiranylquinolin-2-one (obtainable by reduction of "B" with $NaBH_4$ to give 6-(2-chloro-1-hydroxyethyl)-1,2,3,4-tetrahydroquinolin-2-one and subsequent treatment with triethylamine in ethanol at 20°), 17.5 g of 3R-benzylpiperidine, 15 g of triethylamine and 1000 ml of ethanol is boiled for 2 hours. After cooling, customary working up gives 6-(2-(3R-benzylpiperidino)-1-hydroxyethyl)-1,2,3,4-tetrahydroquinolin-2-one ((R)-"C"), m.p. 136°–138°.

Example 6

6-(3-Chloro-1-oxopropyl)-1,2,3,4-tetrahydroquinazolin-2-one 20 g of aluminium chloride (0.15 mol) are taken up in 100 ml of dichloromethane. 7.43 g of 1,2,3,4-tetrahydroquinazolin-2-one (0.05 mol) are added in portions with stirring at a maximum of 20° C. The reaction mixture thus obtained is subsequently stirred for 30 minutes. A solution consisting of 6.98 g of 3-chloropropionyl chloride (0.055 mol) and 50 ml of dichloromethane is then added dropwise with stirring at a temperature of at most 25° C. and the mixture is subsequently stirred for a further hour. After completion of the reaction, the reaction mixture obtained is stirred into 300 g of ice, and the precipitate is filtered off with suction and washed with plenty of water and small amounts of methanol. The reaction forms a slightly more polar product than the starting material, which can be separated by thin-layer chromatography using an eluent consisting of chloroform and methanol in the mixture ratio 95:5. Yield: 11.37 g of 6-(3-chloro-1-oxopropyl)-1,2,3,4-tetrahydroquinazolin-2-one (95.3% of theory); m.p: >270° C.

Example 7

5-(3-Chloro-1-oxopropyl)-6-chloro-2,3-dihydrobenzimidazol-2-one 44.68 g of aluminium chloride (0.335 mol) are initially introduced into a reaction flask. 4.9 ml of DMF are slowly added dropwise with stirring, the temperature rising to approximately 56° C. 6.9 ml of 3-chloropropionyl chloride (0.072 mol) are added to this mixture. 8.07 g of 6-chloro-2,3-dihydrobenzimidazol-2-one (0.048 mol) are then slowly added in portions and the mixture is stirred at 80° C. for one hour. After completion of the reaction the reaction mixture obtained is stirred into 400 g of ice, and the precipitate is filtered off with suction and washed with plenty of water and small amounts of acetone. The reaction leads to a slightly more non-polar product which can be separated by thin-layer chromatography using an eluent consisting of-chloroform and methanol in the mixture ratio 9:1. Yield: 9.72 g of 5-(3-chloro-1-oxopropyl)-6-chloro-2,3-dihydrobenzimidazol-2-one (78.2% of theory); m.p.: 201°–204° C.

Example 8

6-{3-[4-(4-Fluorobenzyl)-1-piperidyl]-1-oxopropyl}-1,2,3, 4-tetrahydroquinazolin-2-one 2.39 g of 6-(3-chloro-1-oxopropyl)-1,2,3,4-tetrahydroquinazolin-2-one (0.01 mol), 40 ml of acetonitrile, 2.30 g of 4-(4-fluorobenzyl)piperidine (0.01 mol) and 4.05 g of triethylamine (0.04 mol) are stirred at room temperature for two hours. The reaction leads to a slightly more nonpolar product than 4-(4-fluorobenzyl)piperidine, which can be separated by thin-layer chromatography using an eluent consisting of chloroform and methanol in the mixture ratio 9:1. After completion of the reaction, the reaction mixture is diluted with water, and the precipitate is filtered off with suction and washed with acetone. The product obtained is then purified by chromatography on a silica gel column, whereby the reaction product is obtained in the form of colourless crystals which are recrystallized again from a methanol/diethyl ether mixture. Yield: 2.43 g of 6-{3-[4-(4-fluorobenzyl)-1-piperidyl]-1-oxopropyl}-1,2,3,4-tetrahydroquinazolin-2-one (61.5% of theory); m.p. 206°–208° C.

The following compounds were additionally prepared analogously:

from 5-(3-chloro-1-oxopropyl)-2,3-dihydro-1H-benzimidazol-2-one and 4-(4-fluorobenzyl)piperidine 5-{3-[4-(4-fluorobenzyl)piperidino]-1-oxopropyl}-2,3-dihydro-1H-benzimidazol-2-one, m.p. 187°–190° C.

from 5-(3-chloro-1-oxopropyl)-2,3-dihydroindol-2-one and 4-(4-fluorobenzyl)piperidine 5-{3-[4-(4-fluorobenzyl)-1-piperidyl]-1-oxopropyl}-2,3-dihydroindol-2-one, m.p. 172°–173° C.

from 7-chloro-6-(3-chloro-1-oxopropyl)-1,2,3,4-tetrahydroquinolin-2-one and 4-(4-fluorobenzyl)piperidine 6-(3-(4-(4-fluorobenzyl)-1-piperidyl)-1-oxopropyl)-7-chloro-1,2,3,4-tetrahydroquinolin-2-one, m.p. 151°–156° C.

from 5-fluoro-6-(3-chloro-1-oxopropyl)-1H-2,3-dihydrobenzimidazol-2-one and 4-(4-fluoro-benzyl)piperidine 5-[3-[4-(4-fluorobenzyl)-1-piperidyl]-1-oxopropyl]-6-fluoro-2,3-dihydro-1H-benzimidazol-2-one, m.p. 197°–199° C.

from 6-(3-chloro-1-oxopropyl)-3-methyl-2,3-dihydrobenzoxazol-2-one and 4-benzylpiperidine 6-[3-(4-benzyl-1-piperidyl)-1-oxopropyl]-2,3-dihydro-3-methylbenzoxazol-2-one, m.p. 131°–132° C.

from 7-chloro-6-(3-chloro-1-oxopropyl)-1,2,3,4-tetrahydroquinolin-2-one and 4-benzylpiperidine 6-(3-(4-benzyl-1-piperidyl)-1-oxopropyl)-7-chloro1,2,3,4-tetrahydroquinolin-2-one, m.p. 146°–147° C.

Example 9

6-{3-4-(4-Fluorobenzyl)-1-piperidyl-1-hydroxypropyl}-1,2,3,4-tetrahydroquinazolin-2-one 1.60 g of 6-{3-[4-(4-fluorobenzyl)-1-piperidyl]-1-oxopropyl}-1,2,3,4-tetrahydroquinazolin-2-one (0.00405 mol) are suspended in 20 ml of methanol, and while stirring and cooling with an ice/water mixture 0.15 g of NaBH$_4$ (0.00405 mol) is added in portions. The mixture is subsequently stirred at room temperature for 16 hours. To complete the reaction of the starting materials, further NaBH$_4$ is subsequently added in small portions. The reaction mixture is then diluted with approximately 50 ml of water, and the precipitate formed is filtered off with suction, washed with water and recrystallized from a methanol/water mixture. Yield: 1.11 g of 6-{3-[4-(4-fluorobenzyl)-1-piperidy]-1-hydroxypropyl}-1,2,3,4-tetrahydroquinazoline-2-one (68.9% of theory); m.p.: 183°–185° C.

The following compounds were additionally prepared analogously:

from 7-(3-(4-benzyl-1-piperidyl)-1-oxopropyl-3,4-dihydro-2H,1,4-benzoxazin-3-one and NaBH$_4$ 7-(3-(4-benzyl-1-piperidyl)-1-hydroxypropyl)-3,4-dihydro-2H-1,4-benzoxazin-3-one, m.p. 182°–183° C.

from (−)-5-{3-[(3R)-3-benzylpiperidino]-1-oxopropyl}-2,3-dihydro-1H-benzimidazol-2-one and NaBH$_4$ (−)-5-{3-[(3R)-3-benzylpiperidino]-1-hydroxypropyl}-2,3-dihydro-1H-benzimidazol-2-one, decomposition from 95° C.

from (+)5-{3-[(3S)-3-benzylpiperidino]-1-oxopropyl}-2,3-dihydro-1H-benzimidazol-2-one and NaBH$_4$ (+)5-{3-[(3S)-3-benzylpiperidino]-1-hydroxypropyl}-2,3-dihydro-1H-benzimidazol-2-one, decomposition from 96° C.

from 5-[3-(4-benzylpiperidino)-1-oxopropyl]-2,3-dihydroindol-2-one and NaBH$_4$ 5-[3-(4-benzylpiperidino)-1-hydroxypropyl]-2,3-dihydroindol-2-one, m.p. 127°–129° C.

from (−)-5-{3-[(3R)-2-benzylpiperidino]-1-oxopropyl}-2,3-dihydroindol-2-one and NaBH$_4$ (−)-5-{3-[(3R)-2-benzylpiperidino]-1-hydroxypropyl}-2,3-dihydroindol-2-one, m.p. 160°–164° C.

from (+)-5-{3-[(3S)-3-benzylpiperidino]-1-oxopropyl}-2,3-dihydroindol-2-one and NaBH$_4$ (+)-5-{3-[(3S)-3-benzylpiperidino]-1-hydroxypropyl}-2,3-dihydroindol-2-one, m.p. 160°–164° C.

from 6-[3-(4-benzyl-1-piperidinyl)-1-oxopropyl]-1,2,3-tetrahydroquinazolin-2-one and NaBH$_4$ 6-[3-(4-benzyl-1-piperidinyl)-1-hydroxypropyl]-1,2,3-tetrahydroquinazolin-2-one, m.p. 146°–149° C.

from (−)-6-{3-[(3R)-3-benzyl-1-piperidyl]-1-oxopropyl}-1,2,3,4-tetrahydroquinazolin-2-one and NaBH$_4$ (−)-6-{3-[(3R)-3-benzyl-1-piperidyl]-1-hydroxypropyl}-1,2,3,4-tetrahydroquinazolin-2-one, m.p. 130°–133° C.

from 6-[3-(4-benzyl-1-piperidinyl)-1-oxopropyl]-8-chloro-4,4-dimethyl-1,2,3,4-tetrahydroquinolin-2-one and NaBH$_4$ 6-[3-(4-benzyl-1-piperidinyl)-1-hydroxypropyl]-8-chloro-4,4-dimethyl-1,2,3,4-tetrahydroquinolin-2-one, m.p. 93°–95° C.

from (+)-6-{3-[(3S)-2-benzyl-1-piperidyl]-1-oxopropyl}-1,2,3,4-tetrahydroquinazolin-2-one and NaBH$_4$ (+)-6-{3-[(3S)-2-benzyl-1-piperidyl]-1-hydroxypropyl}-1,2,3,4-tetrahydroquinazolin-2-one, m.p. 128°–130° C.

from 6-{3-[(3R)-3-benzyl-1-piperidyl]-1-oxopropyl}-8-chloro-4,4-dimethyl-1,2,3,4-tetrahydroquinolin-2-one and NaBH$_4$ 6-{3-[(3R)-3-benzyl-1-piperidyl]-1-hydroxypropyl}-8-chloro-4,4-dimethyl-1,2,3,4-tetrahydroquinolin-2-one, resin from 6-{3-[(3S)-3-benzyl-1-piperidyl]-1-oxopropyl}-8-chloro-4,4-dimethyl-1,2,3,4-tetrahydroquinolin-2-one and NaBH$_4$ 6-{3-[(3S)-3-benzyl-1-piperidyl]-1-hydroxypropyl}-8-chloro-4,4-dimethyl-1,2,3,4-tetrahydroquinolin- 2-one, resin from 7-(3-((3S)-3-benzyl-1-piperidyl)-1-oxopropyl)-3,4-dihydro-2H-1,4-benzoxazin-3-one and NaBH$_4$ 7-(3-((3S)-3-benzyl-1-piperidyl)-1-hydroxypropyl)-3,4-dihydro-2H-1,4-benzoxazin-3-one, m.p. 128°–132° C.

from 7-(3-((3R)-3-benzyl-1-piperidyl)-1-oxopropyl)-3,4-dihydro-2H-1,4-benzoxazin-3-one and NaBH$_4$ 7-(3-((3R)-3-benzyl-1-piperidyl)-1-hydroxypropyl)-3,4-dihydro-2H-1,4-benzoxazin-3-one, m.p. 132°–140° C.

from 6-[3-(4-benzylpiperidino)-1-oxopropyl]-5-chloro-2,3-dihydrobenzoxazol-2-one and NaBH$_4$ 6-[3-(4-benzylpiperidino)-1-hydroxypropyl]-5-chloro-2,3-dihydrobenzoxazol-2-one, decomposition from 94° C.

from (−)-6-{3-[(3R)-3-benzylpiperidino]-1-oxopropyl}-5-chloro-2,3-dihydrobenzoxazol-2-one and NaBH$_4$ (−)-6-{3-[(3R)-3-benzylpiperidino]-1-hydroxypropyl}-5-chloro-2,3-dihydrobenzoxazol-2-one, decomposition from 98° C.

from (+)-6-{3-[(3S)-3-benzylpiperidino]-1-oxopropyl}-5-chloro-2,3-dihydrobenzoxazol-2-one and NaBH₄ (+)-6-{3-[(3S)-3-benzylpiperidino]-1-hydroxypropyl}-5-chloro-2,3-dihydrobenzoxazol-2-one, decomposition from 98° C.

from 6-[3-(4-benzyl-1-piperidyl)-1-oxopropyl]-1,2,3,4-tetrahydroquinolin-2-one and NaBH₄ 6-[3-(4-benzyl-1-piperidyl)-1-hydroxypropyl]-1,2,3,4-tetrahydroquinolin-2-one, m.p. 137°–138° C.

from 6-(3-(4-benzyl-1-piperidinyl)-1-oxopropyl)-7-chloro-1,2,3,4-tetrahydroquinolin-2-one and NaBH₄ 6-(3-(4-benzyl-1-piperidinyl)-1-hydroxypropyl)-7-chloro-1,2,3,4-tetrahydroquinolin-2-one, m.p. 181°–184° C.

from (−)-6-{3-[(3R)-3-benzyl-1-piperidyl]-1-oxopropyl}-1,2,3,4-tetrahydroquinolin-2-one and NaBH₄ (−)-6-{3-[(3R)-3-benzyl-1-piperidyl]-1-hydroxypropyl}-1,2,3,4-tetrahydroquinolin-2-one, m.p. 182° C.

from 6-{3-[(3S)-3-benzyl-1-piperidyl]-1-oxopropyl}-1,2,3,4-tetrahydroquinolin-2-one and NaBH₄ 6-{3-[(3S)-3-benzyl-1-piperidyl]-1-hydroxypropyl}-1,2,3,4-tetrahydroquinolin-2-one, m.p. 182°–185° C.

from (+)-6-((3S)-3-benzyl-1-piperidinyl)-1-oxopropyl)-7-chloro-1,2,3,4-tetrahydroquinolin-2-one and NaBH₄ (+)-6-((3S)-3-benzyl-1-piperidinyl)-1-hydroxypropyl)-7-chloro-1,2,3,4-tetrahydroquinolin-2-one, m.p. 123°–125° C.

from (−)-6-((3R)-3-benzyl-1-piperidinyl)-1-oxopropyl)-7-chloro-1,2,3,4-tetrahydroquinolin-2-one and NaBH₄ (−)-6-((3R)-3-benzyl-1-piperidinyl)-1-hydroxypropyl)-7-chloro-1,2,3,4-tetrahydroquinolin-2-one, m.p. 122°–125° C.

from 6-(3-(4-benzyl-1-piperidyl)-1-oxoethyl)-5-chloro-1,2,3,4-tetrahydroquinolin-2-one and NaBH₄ 6-(3-(4-benzyl-1-piperidyl)-1-hydroxyethyl)-5-chloro-1,2,3,4-tetrahydroquinolin-2-one, m.p. 224°–227° C.

from 5-{3-[4-(4-fluorobenzyl)-piperidino]-1-oxopropyl}-2,3-dihydro-1H-benzimidazol-2-one and NaBH₄ 5-{3-[4-(4-fluorobenzyl)piperidino]-1-hydroxypropyl}-2,3-dihydro-1H-benzimidazol-2-one, m.p. 218°–221° C.

from 5-[3-(4-benzyl-1-piperidyl)-1-oxopropyl]-6-chloro-2,3-dihydro-1H-benzimidazol-2-one and NaBH₄ 5-[3-(4-benzyl-1-piperidyl)-1-hydroxypropyl]-6-chloro-2,3-dihydro-1H-benzimidazol-2-one, m.p. 233°–236° C.

from (−)-5-{[3-(3R)-3-benzyl-1-piperidyl]-1-oxopropyl}-6-chloro-2,3-dihydro-1H-benzimidazol-2-one and NaBH₄ (−)-5-{[3-(3R)-3-benzyl-1-piperidyl]-1-hydroxypropyl}-6-chloro-2,3-dihydro-1H-benzimidazol-2-one, decomposition from 115° C.

from (+)-5-{3-[(3S)-3-benzyl-1-piperidyl]-1-oxopropyl}-6-chloro-2,3-dihydro-1H-benzimidazol-2-one and NaBH₄ (+)-5-{3-[(3S)-3-benzyl-1-piperidyl]-1-hydroxypropyl}-6-chloro-2,3-dihydro-1H-benzimidazol-2-one, decomposition from 94° C.

from 6-chloro-5-{3-[4-(4-fluorobenzyl)-1-piperidyl]-1-oxopropyl}-2,3-dihydro-1H-benzimidazol-2-one and NaBH₄ 6-chloro-5-{3-[4-(4-fluorobenzyl)-1-piperidyl]-1-hydroxypropyl}-2,3-dihydro-1H-benzimidazol-2-one, m.p. 246°–248° C.

from 6-[3-(4-benzyl-1-piperidyl)-1-oxopropyl]-2,3-dihydrobenzoxazol-2-one and NaBH₄ 6-[3-(4-benzyl-1-piperidyl)-1-hydroxypropyl]-2,3-dihydrobenzoxazol-2-one, m.p. 177°–178° C.

from 5-{3-[4-(4-fluorobenzyl)-1-piperidyl]-1-oxopropyl}-2,3-dihydroindol-2-one and NaBH₄ 5-{3-[4-(4-fluorobenzyl)-1-piperidyl]-1-hydroxypropyl}-2,3-dihydroindol-2-one, m.p. 154°–155° C.

from 7-[3-(4-benzyl-1-piperidyl)-1-oxopropyl]-2,3,4,5-tetrahydro-1H-1-benzazepin-2-one and NaBH₄ 7-[3-(4-benzyl-1-piperidyl)-1-hydroxypropyl]-2,3,4,5-tetrahydro-1H-1-benzazepin-2-one, m.p. 140°–141° C.

from 6-(3-(4-fluorobenzyl-1-piperidyl)-1-oxopropyl)-7-chloro-1,2,3,4-tetrahydroquinolin-2-one and NaBH₄ 6-(3-(4-fluorobenzyl-1-piperidyl)-1-hydroxypropyl)-7-chloro-1,2,3,4-tetrahydroquinolin-2-one, m.p. 220°–222° C.

from 7-{3-[(3R)-3-benzyl-1-piperidyl]-1-oxopropyl}-2,3,4,5-tetrahydro-1H-1-benzazepin-2-one and NaBH₄ 7-{3-[(3R)-3-benzyl-1-piperidyl]-1-hydroxypropyl}-2,3,4,5-tetrahydro-1H-1-benzazepin-2-one, resin from (−)-6-{2-[(3S)-3-benzylpiperidino]-1-oxoethyl]-5-chloro-2,3-dihydrobenzoxazol-2-one and NaBH₄ (−)-6-{2-[(3S)-3-benzylpiperidino]-1-hydroxyethyl]-5-chloro-2,3-dihydrobenzoxazol-2-one-hydrochloride, decomposition from 147° C.

from (+)-6-{2-[(3R)-3-benzylpiperidino]-1-oxoethyl]-5-chloro-2,3-dihydrobenzoxazol-2-one and NaBH₄ (+)-6-{2-[(3R)-3-benzylpiperidino]-1-hydroxyethyl]-5-chloro-2,3-dihydrobenzoxazol-2-one-hydrochloride, decomposition from 144° C.

from (+)-6-{2-[(3S)-3-benzyl-1-piperidyl]-1-oxo-ethyl]-7-chloro-1,2,3,4-tetrahydroquinolin-2-one and NaBH₄ (+)-6-(2-((3S)-3-benzyl-1-piperidyl)-1-hydroxyethyl)-7-chloro-1,2,3,4-tetrahydroquinolin-2-one, decomposition from 107°–117° C.

from (−)-6-(2-((3R)-3-benzyl-1-piperidyl)-1-oxoethyl)-7-chloro-1,2,3,4-tetrahydroquinolin-2-one and NaBH₄ (−)-6-(2-((3R)-3-benzyl-1-piperidyl)-1-hydroxyethyl)-7-chloro-1,2,3,4-tetrahydroquinolin-2-one, amorphous from 7-[2-(4-benzyl-1-piperidyl)-1-oxoethyl]-2,3,4,5-tetrahydro-1H-1-benzazepin-2-one and NaBH₄ 7-[2-(4-benzyl-1-piperidyl)-1-hydroxyethyl]-2,3,4,5-tetrahydro-1H-1-benzazepin-2-one-hydrochloride, decomposition from 238°–239° C.

from (−)-7-{2-[(3R)-3-benzyl-1-piperidyl]-1-oxoethyl}-2,3,4,5-tetrahydro-1H-1-benzazepin-2-one and NaBH₄ (−)-7-{2-[(3R)-3-benzyl-1-piperidyl]-1-hydroxyethyl}-2,3,4,5-tetrahydro-1H-1-benzazepin-2-one dihydrochloride hydrate, m.p. 115°–118° C.

from (+)-7-{2-[(3s)-3-benzyl-1-piperidyl]-1-oxoethyl}-2,3,4,5-tetrahydro-1H-1-benzazepin-2-one and NaBH₄ (+)-7-{2-[(3S)-3-benzyl-1-piperidyl]-1-hydroxyethyl}-2,3,4,5-tetrahydro-1H-1-benzazepin-2-one dihydrochloride hydrate, m.p. 115°–118° C.

from (+)-6-(2-((3S)-3-benzyl-1-piperidyl)-1-oxo-ethyl-5-chloro-1,2,3,4-tetrahydroquinolin-2-one and NaBH₄ (+)-6-(2-((3S)-3-benzyl-1-piperidyl)-1-hydroxyethyl)-5-chloro-1,2,3,4-tetrahydroquinolin-2-one, m.p. 119°–120° C.

from (−)-6-(2-((3R)-3-benzyl-1-piperidyl)-1-oxoethyl)-5-chloro-1,2,3,4-tetrahydroquinolin-2-one and NaBH₄ (−)-6-(2-((3R)-3-benzyl-1-piperidyl)-1-hydroxyethyl)-5-chloro-1,2,3,4-tetrahydroquinolin-2-one, m.p. 119°–125° C.

from 5-[3-(4-benzyl-1-piperidyl)-1-oxopropyl]-6-fluoro-2,3-dihydro-1H-benzimidazol-2-one and NaBH₄ 5-[3-

(4-benzyl-1-piperidyl)-1-hydroxypropyl]-6-fluoro-2,3-dihydro-1H-benzimidazol-2-one, m.p. 244°–247° C.

from (−)-5-{3-[(3R)-3-benzyl-1-piperidyl]-1-oxopropyl}-6-fluoro-2,3-dihydro-1H-benzimidazol-2-one and NaBH$_4$ (−)-5-{3-[(3R)-3-benzyl-1-piperidyl]-1-hydroxypropyl}-6-fluoro-2,3-dihydro-1H-benzimidazol-2-one, [d]D$^{20}$=−15.1° (DMSO)

from (+)-5-{3-[(3S)-3-benzyl-1-piperidyl]-1-oxopropyl}-6-fluoro-2,3-dihydro-1H-benzimidazol-2-one and NaBH$_4$ (+)-5-{3-[(3S)-3-benzyl-1-piperidyl]-1-hydroxypropyl}-6-fluoro-2,3-dihydro-1H-benzimidazol-2-one, [d]D$^{20}$=−15.8° (DMSO)

from 5-{3-[4-(4-fluorobenzyl)-1-piperidyl]-1-oxopropyl}-6-fluoro-2,3-dihydro-1H-benzimidazol-2-one and NaBH$_4$ 5-{3-[4-(4-fluorobenzyl)-1-piperidyl]-1-hydroxypropyl}-6-fluoro-2,3-dihydro-1H-benzimidazol- 2-one, m.p. 202°–205° C.

Example 10

5-[3-(4-Benzyl-1-piperidyl)-1-oxopropyl]-2,3-dihydrobenzimidazol-2-one a) 2.25 g (0.01 mol) of 5-(3-chloro-1-oxopropyl)-2,3-dihydrobenzimidazol-2-one prepared analogously to Example 6 are taken up in 40 ml of acetonitrile. 1.75 g of 4-benzylpiperidine (0.01 mol) and 3.04 g of triethylamine (0.03 mol) are added to this mixture with stirring. The reaction mixture obtained is stirred at room temperature for two hours. The reaction solution is subsequently diluted with 100 ml of dichloromethane and shaken with 70 ml of water. The phases are separated. After drying the organic phase, the solvent is distilled off in vacuo.

Yield: 3.64 g of 5-[3-(4-benzyl-1-piperidyl)-1-oxopropyl]-2,3-dihydrobenzimidazol-2-one.

b) The reaction is carried out as in a), but the precipitate formed in the reaction is filtered off with suction and washed several times with water. The crude product is then dissolved in 200 ml of dichloromethane and 10 ml of methanol. The solution is filtered and dried. After drying, the solvent mixture is distilled off in vacuo. The residue thus obtained is separated by chromatography on a silica gel column using a dichloromethane/methanol mixture as an eluent, non-polar impurities being obtained in addition to the reaction product. The reaction product obtained in the form of yellow crystals is boiled in acetone and recrystallized.

Yield: 1.52 g of 5-[3-(4-benzyl-1-piperidyl)-1-oxopropyl]-2,3-dihydrobenzimidazol-2-one (41.9% of theory); m.p.: 183°–186° C.

The following compounds were additionally prepared analogously:

from 6-(3-chloro-1-oxopropyl)-2,3-dihydroxybenzoxazol-2-one and 4-benzylpiperidine 6-[3-(4-benzyl-1-piperidyl)-1-oxopropyl]-2,3-dihydrobenzoxazol-2-one, m.p. 161°–162° C.

from 7-(3-chloro-1-oxopropyl)-2,3,4,5-tetrahydro-1H-1-benzazepin-2-one and 4-benzylpiperidine 7-[3-(4-benzyl-1-piperidyl)-1-oxopropyl]-2,3,4,5-tetrahydro-1H-1-benzazepin-2-on, resin from 7-(3-chloro-1-oxopropyl)-2,3,4,5-tetrahydro-1H-1-benzazepin-2-one and 3-R-benzylpiperidine 7-{3-[(3R)-3-benzyl-1-piperidyl]-1-oxopropyl}-2,3,4,5-tetrahydro-1H-1-benzazepin-2-one, resin from 6-fluoro-5-(3-chloro-1-oxopropyl)-2,3-dihydro-1H-benzimidazol-2-one and 4-benzylpiperidine 5-[3-(4-benzyl-1-piperidyl)-1-oxopropyl]-6-fluoro-2,3-dihydro-1H-benzimidazol-2-one, m.p. 205°–206° C.

from 5-(3-chloro-1-oxopropyl)-2,3-dihydro-1-methylbenzimidazol-2-one and 4-benzylpiperidine 5-[3-(4-benzyl-1-piperidinyl)-1-oxopropyl]-2,3-dihydro-1-methyl-benzimidazol-2-one, m.p. 154°–157° C.

from 6-fluoro-5-(3-chloro-1-oxopropyl)-1H-2,3-dihydrobenzimidazol-2-one and 3-R-benzyl-piperidine (−)-5-{3-[(3R)-3-benzyl-1-piperidyl]-1-oxopropyl}-6-fluoro-2,3-dihydro-1H-benzimidazol-2-one, m.p. 193°–194° C.

from 6-fluoro-5-(3-chloro-1-oxopropyl)-1H-2,3-dihydrobenzimidazol-2-one and 3-S-benzyl-piperidine (+)-5-{3-[(3S)-3-benzyl-1-piperidyl]-1-oxopropyl}-6-fluoro-2,3-dihydro-1H-benzimidazol-2-one, m.p. 192°–194° C.

from 6-(3-chloro-1-oxopropyl)-1,2,3,4-tetrahydroquinazolin-2-one and 4-benzylpiperidine 6-[3-(4-benzyl-1-piperidyl)-1-oxopropyl]-1,2,3,4-tetrahydroquinazolin-2-one, m.p. 196°–199° C.

from 6-(3-chloro-1-oxopropyl)-2,3-dihydrobenzoxazole and 4-(4-fluorobenzyl)piperidine 6-{3-[4-(4-fluorobenzyl)-1-piperidyl]-1-oxopropyl}-2,3-dihydrobenzoxazol-2-one, m.p. 168°–173° C.

Example 11

5-[3-(4-Benzyl-1-piperidyl)-1-hydroxypropyl]-2,3-dihydro-2-oxo-benzimidazole 3.64 g (0.01 mol) of the reaction product from Example 10 are suspended in 40 ml of methanol. 0.38 g of NaBH$_4$ (0.01 mol) is added to this suspension in portions while stirring and cooling with an ice/water mixture. The mixture is subsequently stirred at room temperature for one hour. The reaction mixture obtained is diluted with 60 ml of water and stirred for a further 30 minutes. The precipitate formed is filtered off with suction and boiled with 50 ml of methanol until fine pale yellow crystals have formed. The crystals are filtered off with suction and washed with diethyl ether. Yield: 2.34 g of 5-[3-(4-benzyl-1-piperidyl)-1-hydroxypropyl]-2,3-dihydro-2-oxo-benzimidazole (64.1% of theory); m.p.: 240°–244° C.

The examples below relate to pharmaceutical preparations.

Example A

Injection vials

A solution of 100 g of an active compound of the formula I and 5 g of disodium hydrogen phosphate in 3 l of double-distilled water is adjusted to pH 6.5 using 2N hydrochloric acid, sterilized by filtration, filled into injection vials, lyophilized under sterile conditions and aseptically sealed. Each injection vial contains 5 mg of active compound.

Example B

Suppositories

A mixture of 20 g of an active compound of the formula I is melted with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of NaH$_2$PO$_4$×2 H$_2$O, 28.48 g of Na$_2$HPO$_4$×12 H$_2$O and 0.1 g of benzalkonium chloride in 940 ml of double-distilled water. The solution is adjusted to pH 6.8, made up to 1 l and sterilized by irradiation. This solution can be used, for example, in the form of eye drops.

Example D

Ointment 500 mg of an active compound of the formula I is mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

Example F

Coated tablets

Analogously to Example E, tablets are pressed which are then coated in a customary manner with a coating of sucrose, potato starch, talc, tragacanth and colorant.

Example G

Capsules 2 kg of active compound of the formula I are filled into hard gelatin capsules in a customary manner such that each capsule contains 20 mg of the active compound.

Example H

Ampoules

A solution of 1 kg of active compound of the formula I in 60 l of double-distilled water is sterilized by filtration, filled into ampoules, lyophilized under sterile conditions and aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A benzylpiperidine compound of formula I

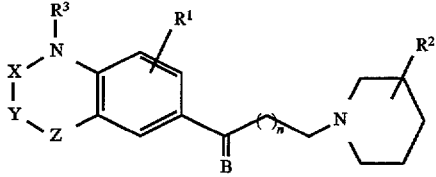

(I)

in which $R^1$ is H, Hal or nitro, $R^2$ is a benzyl group, which is unsubstituted or substituted by Hal on the aromatic ring, in the 2-, 3- or 4-position of the piperidine ring, with the proviso that $R^2$ is not in the 4-position if X is —CO—, Y and Z are —CH$_2$— and $R^1$ is H, or X is —CO—, Y is —CH$_2$—, Z is a bond, and $R^1$ is H, $R^3$ is H or A, X is —O—, —S—, —NH—, —CO— or —SO$_2$—, Y is —CH$_2$—, —O—, —S—, —NH— or alternatively —CO— if X is —CO— and Z is —NH— or —NA—, Z is —CH$_2$—, —C(A)$_2$—, —CH$_2$CH$_2$—, —CH=CH—, —CO—, —NH—, —NA—, —O—, —S— or a bond, wherein X—Y or Y—Z is not —O—O—, —S—S—, —NH—O—, —O—NH—, —NH—NH—, —O—S— or —S—O—, A is alkyl having 1–6 C atoms, B is O or both H and OH, Hal is F, Cl, Br or I and n is 1 or 2 or a physiologically acceptable salt thereof.

2. A compound according to claim 1, of formula Ia, wherein $R^1$ is H.

3. A compound according to claim 1, of formula Ib, wherein $R^1$ is H or Cl.

4. A compound according to claim 1, of formula Ic, wherein X—Y—Z is —CO—NH—, —CO—CH$_2$—CH$_2$—, —CO—CH$_2$—C(CH$_3$)$_2$—, —CO—CH$_2$—O—, —CO—O—CH$_2$—, —CO—NH—CH$_2$—, —CO—O—, —CO—S— or —CO—CH$_2$—.

5. A compound according to claim 1, of formula Id, wherein X—Y—Z is —CO—NH—, —CO—CH$_2$—CH$_2$—, or —CO—CH$_2$—C(CH$_3$)$_2$—.

6. A compound according to claim 1, of formula Ie, wherein X—Y—Z is —CO—NH—, or —CO—CH$_2$—CH$_2$—.

7. A compound according to claim 1, of formula If, wherein $R^1$ is H or Cl and X—Y—Z is —CO—NH—, —CO—CH$_2$—CH$_2$—, or —CO—CH$_2$—C(CH$_3$)$_2$—.

8. A compound according to claim 1, of formula Ig, wherein $R^1$ is H or Cl and X—Y—Z is —CO—NH—, or —CO—CH$_2$—CH$_2$—.

9. A compound according to claim 1, of formula Ih, wherein $R^1$ is H and X—Y—Z is —CO—NH—.

10. A compound according to claim 1, which is
   (a) 1,2,3,4-Tetrahydro-6-(1-hydroxy-2-(3-benzylpiperidino)ethyl)quinolin-2-one, a diastereomer thereof, an enantiomer thereof, or a salt thereof;
   (b) 5-[3-(4-Benzylpiperidino)-1-hydroxypropyl]-2,3-dihydro-2-oxo-1H-benzimidazole; or
   (c) 5-{3-[4-(4-Fluorobenzyl)piperidino]-1-oxo-propyl}-2,3-dihydro-1H-benzimidazol-2-one.

11. A pharmaceutical composition comprising at least one compound of formula I according to claim 1 or a physiologically acceptable salt thereof, and a pharmaceutically acceptable carrier.

12. A process for the treatment of ischaemia, pain, epilepsy, schizophrenia, Alzheimer's disease, Parkinson's disease, Huntington's disease, cerebral infarction, or psychoses caused by extensive amino acid levels, comprising administering an effective amount of a compound of formula I according claim 1 or a physiologically acceptable salt thereof.

13. A process for the preparation of benzylpiperidine derivatives of the formula I according to claim 1, and of their salts, wherein that a compound of the formula (II)

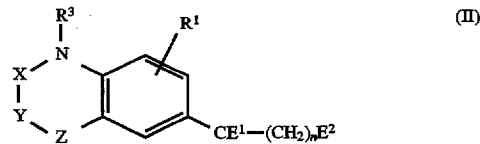

(II)

in which $E^1$ is O or H and OH, $E^2$ is Cl, Br, I or a reactive esterified OH group or $E^1$ and $E^2$ together can be an O atom and
$R^1, R^3, X, Y$
Z and n have the meanings indicated,
is reacted with a compound of the formula III

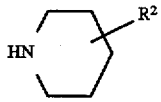 (III)

in which $R^2$ has the meaning indicated, and/or in that a compound which otherwise corresponds to the formula I, but which instead of one or more H atoms contains one or more reducible groups and/or one or more additional bonds, is treated with a reducing agent, and/or in that a base of the formula I which is obtained is converted into one of its acid addition salts by treating with an acid.

14. A process for the production of pharmaceutical preparations, wherein a compound of the formula I according to claim 1 and/or one of its physiologically acceptable salts is brought into a suitable dose form together with at least one solid, liquid or semi-liquid excipient and/or auxiliary.

* * * * *